United States Patent
Inoue (10) Patent No.: US 8,041,092 B2
(45) Date of Patent: Oct. 18, 2011

(54) APPARATUS AND METHOD ADAPTED TO CORRECT IMAGE DATA ACQUIRED BY IMAGE DETECTOR

(75) Inventor: Hitoshi Inoue, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 1034 days.

(21) Appl. No.: 10/441,049

(22) Filed: May 20, 2003

(65) Prior Publication Data

US 2003/0223629 A1 Dec. 4, 2003

(30) Foreign Application Priority Data

May 30, 2002 (JP) .................................. 2002-157551
May 6, 2003 (JP) .................................. 2003-127989

(51) Int. Cl.
*G06K 9/00* (2006.01)

(52) U.S. Cl. ........................................ 382/131

(58) Field of Classification Search ................ 382/128, 382/132, 154, 98.7, 98.8, 131; 378/154, 378/98.7, 98.8, 1.9; 358/1.9; 600/436, 407
See application file for complete search history.

(56) References Cited

U.S. PATENT DOCUMENTS

| | | | |
|---|---|---|---|
| 4,602,291 A | 7/1986 | Temes ........................... | 358/221 |
| 4,789,930 A * | 12/1988 | Sones et al. ................... | 378/207 |
| 4,975,864 A | 12/1990 | Sendall et al. ............ | 364/571.01 |
| 5,237,431 A | 8/1993 | Imoto ........................... | 358/445 |
| 5,321,811 A | 6/1994 | Kato et al. .................... | 395/166 |
| 5,974,113 A * | 10/1999 | Bruijns et al. ................ | 378/98.7 |
| 6,694,172 B1 * | 2/2004 | Gagnon et al. ............... | 600/436 |
| 7,164,805 B2 * | 1/2007 | Takahira ....................... | 382/263 |
| 2001/0026372 A1 * | 10/2001 | Misawa ........................ | 358/1.9 |
| 2001/0033638 A1 * | 10/2001 | Inoue ............................ | 378/154 |
| 2003/0016855 A1 * | 1/2003 | Shinbata ....................... | 382/132 |
| 2003/0053592 A1 * | 3/2003 | Takahashi et al. .......... | 378/98.8 |

FOREIGN PATENT DOCUMENTS

| | | |
|---|---|---|
| JP | 07-072256 | 3/1995 |
| JP | 09-113836 A | 5/1997 |
| JP | 11-252373 A | 9/1999 |

* cited by examiner

*Primary Examiner* — Vu Le
*Assistant Examiner* — Claire X Wang
(74) *Attorney, Agent, or Firm* — Fitzpatrick, Cella, Harper & Scinto (57) ABSTRACT

An apparatus adapted to correct an image data acquired by an image detector including a plurality of detecting elements, includes: a first correction unit adapted for obtaining an offset-corrected image by removing an offset component due to the image detector from the image data, a second correction unit adapted for correcting a pixel value of the offset-corrected image on the basis of a gain of corresponding one of the plurality of detecting elements; and a third correction unit adapted for correcting a value of a selected pixel of the offset-corrected image, the selected pixel being selected based on the pixel value of the offset-corrected image, by generating a pixel value in place of a value of the selected pixel obtained by said second correction unit.

5 Claims, 8 Drawing Sheets

APPARATUS AND METHOD ADAPTED TO CORRECT IMAGE DATA ACQUIRED BY IMAGE DETECTOR

FIELD OF THE INVENTION

The present invention relates to correction of image data acquired by an image detector.

BACKGROUND OF THE INVENTION

The inside of a matter, particularly a human body, can be visualized by measuring a distribution of radioactive rays, typically X-rays, transmitted through matter such as the human body. A ray distribution such as of X-rays is detected nowadays generally with a large-size image sensor using a solid state image pickup device and called a flat panel X-ray sensor. The merits of a solid state image pickup device reside in that signals indicative of an energy distribution on a plane can be directly and spatially sampled from a plurality of pixel elements disposed on the plane.

The demerits reside in that since each of the plurality of pixel elements to be spatially sampled is fundamentally an independent element and has different characteristics, an acquired image is required to be corrected in accordance with variations in the characteristics among the respective pixel elements.

The main variation in the characteristics of pixel elements as energy conversion elements is a variation in conversion efficiencies (gain) and offset values. The gain and offset are required to be corrected first, if a flat panel X-ray sensor is used as a solid state image pickup device.

Figure 4:
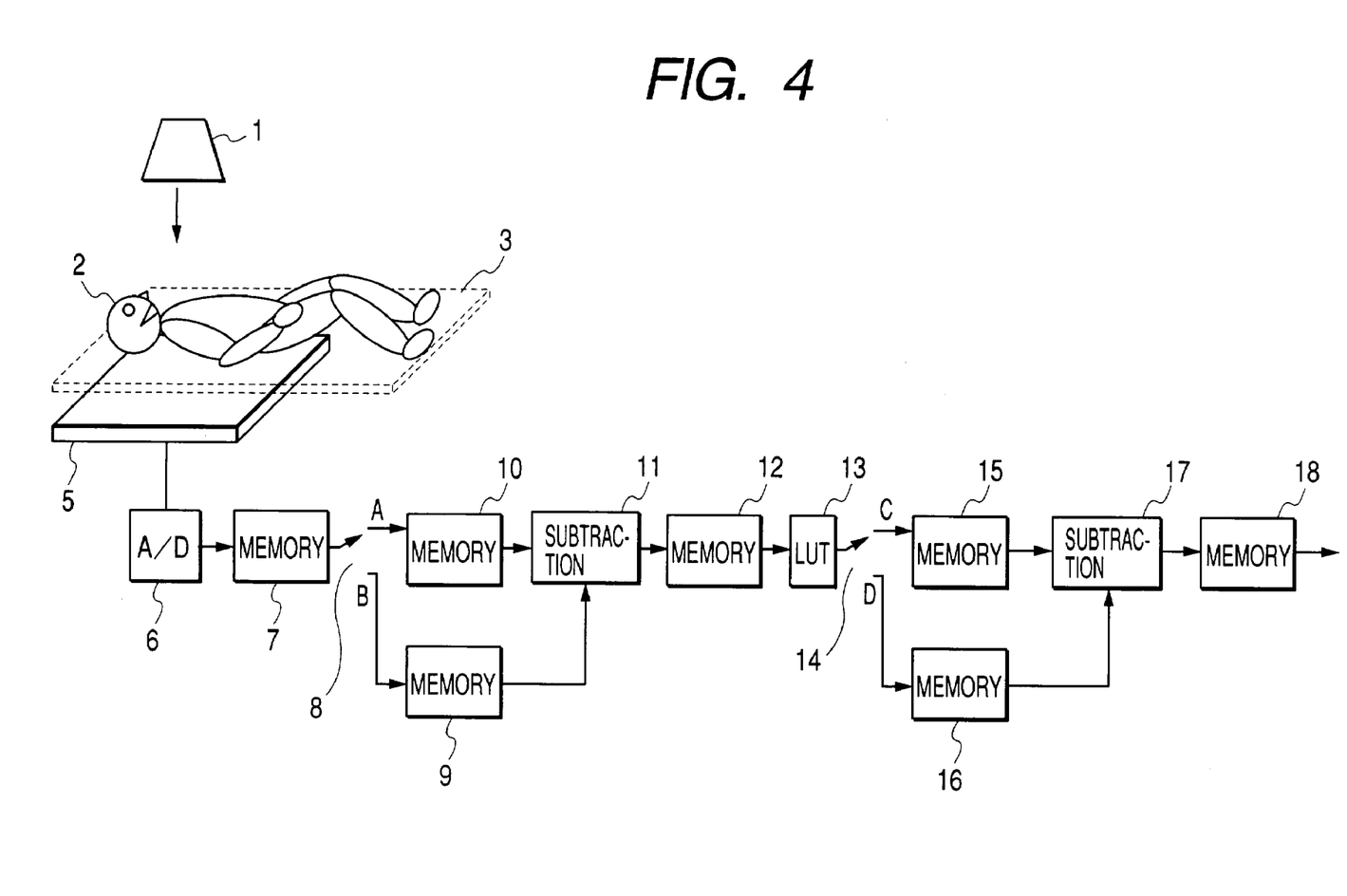
FIG. 4 is a diagram used for explaining prior art technologies.

Description will be given on prior art technologies. FIG. 4 is a schematic block diagram of the apparatus for correcting the gain and offset. In FIG. 4, reference numeral 1 represents an X-ray generating apparatus which is controlled by a controller having a high voltage generator to generate X-rays along a direction indicated by an arrow. An object, typically a human body 2, is on a bed 3. An X-ray image sensor 5 is used for converting an intensity distribution of X-rays transmitted through the object into electric signals. The X-ray image sensor 5 is made of a large-size solid image pickup device. Signals indicative of an X-ray intensity distribution on a two-dimensional plane can be spatially sampled from a plurality of pixel elements disposed in a two-dimensional matrix form.

In the following, this X-ray image sensor is called a flat panel sensor. A sampling pitch is set generally to about 100 µm to 200 µm to image the internal structure of a human body. The flat panel sensor is controlled by the controller (not shown). Pixels are sequentially scanned to convert charges in each pixel into voltage or current. This analog electric signal is supplied to an A/D converter 6, which converts the analog signal into a digital signal.

The A/D converted digital signal is temporarily stored in a memory 7. Data in the memory 7 is stored via a switch 8 into one of two memories 9 and 10. The memory 9 stores an image signal output from the flat panel sensor under no exposure of X-rays, as an offset fixed pattern image. The memory 10 stores an image signal obtained under exposure of X-rays.

Generally an X-ray amount measuring apparatus (also called a phototimer) is used to monitor the X-ray amount transmitted through a subject and control X-ray exposure. When the cumulative X-ray amount reaches a predetermined value, X-ray exposure is stopped. When the X-ray exposure stops, the controller scans the flat panel sensor, and image information of the subject is stored in the memory 10 via the memory 7 and switch 8. Immediately thereafter, the flat panel sensor is driven under no X-ray exposure during the period same as the subject imaging time to accumulate electric charges which are converted into a digital signal and stored in the memory 7 as an offset fixed pattern signal.

This offset fixed pattern signal is stored in the memory 9 via the switch 8 which is turned to its contact B. A subtractor 11 subtracts a value in the memory 9 at each address from a value in the memory 10 at a corresponding address and the subtracted values are stored in a memory 12.

A look-up table (LUT) 13 is a table of logarithmic value conversion used for division operation. A radiation-sensed image of a subject is stored in a memory 15 via LUT 13 and a switch 14 which is turned to a contact C.

A memory 16 stores an image signal subjected to a calibration operation of the apparatus. Also in this case, an image is sensed in the above-described manner and stored via the switch 14 turned to a contact D. In the calibration operation, an X-ray amount distribution itself is sensed without the subject 2 to obtain a variation in gains of pixel elements. The calibration operation is usually performed approximately once per day, for example, at the start of a day work. With this calibration operation, data (also called a gain image) corresponding to a variation in gains of pixel elements of the flat panel sensor is stored in the memory 16.

A subtractor 17 subtracts the gain image from the subject image to generate an image signal whose gain variation is corrected. This image signal is stored in a memory 18. This corrected image signal is subjected to succeeding image diagnosing, filing, transmission, display or the like.

A general radiographic apparatus converts the corrected image signal into a diagnosis image signal by using a gradation process, a dynamic range change process, a spatial frequency process and the like. This diagnosis image signal is supplied to an external apparatus, typically a filing apparatus and a hard copy apparatus.

An X-ray image is characterized in its very wide dynamic range. For example, a medical radiographic image has a low level signal area where X-rays were almost shielded, for example, due to metal embedded in a human body.

Such a low level signal area may be neglected because it is quite insignificant as image information. However, if the gain correction is performed for this low signal level area, the gain variation pattern (gain image) of pixel elements is superposed upon a subject image, although this area corresponds to an area having almost no incidence energy, i.e., an area without a signal level variation. Noises are therefore generated by this gain correction.

Figure 5A:
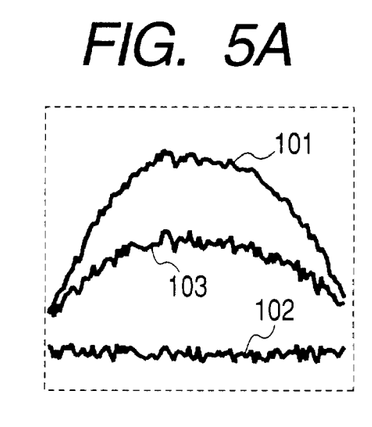
FIGS. 5A, 5B, 5C, 5D, 5E and 5F are diagrams used for explaining the problem to be solved by the invention.
Figure 5B:
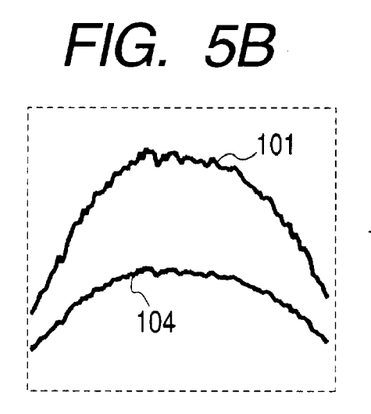
Figure 5C:
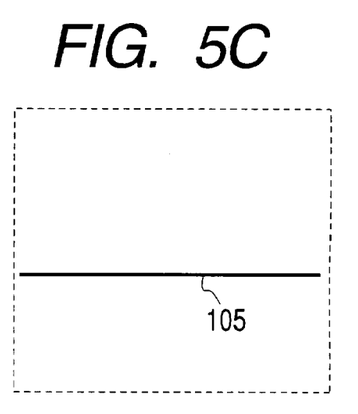

This phenomenon will be described with reference FIGS. 5A, 5B, 5C, 5D, 5E and 5F. FIGS. 5A, 5B and 5C show an image of general X-ray distributions in one-dimensional representation. For the purposes of simplicity, random noises generated during image sensing are omitted. A line 101 represents a gain variation acquired in the calibration operation. A line 102 represents an offset acquired under no X-ray exposure. A line 103 represents an image of an actual subject. It is assumed herein that the subject has a uniform radiation transmission factor distribution. FIG. 5B shows an image 104 after the offset 102 is removed from the image signal 103. FIG. 5C shows an image 105 after gain correction in which the offset-corrected image 104 is divided by the gain variation (gain image) 101. This image 105 has uniform pixel values.

Figure 5D:
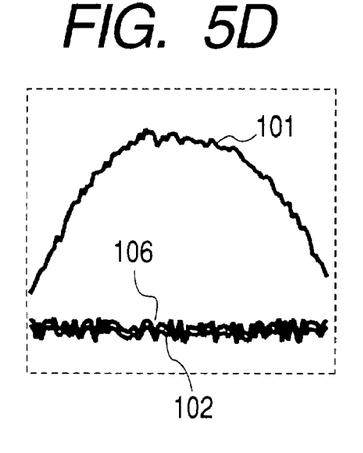
Figure 5E:
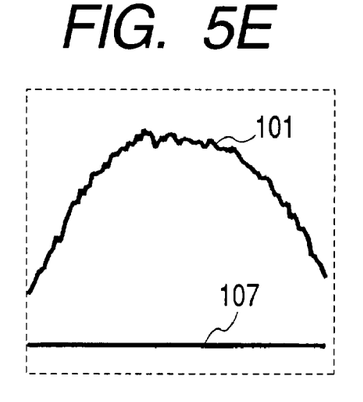
Figure 5F:
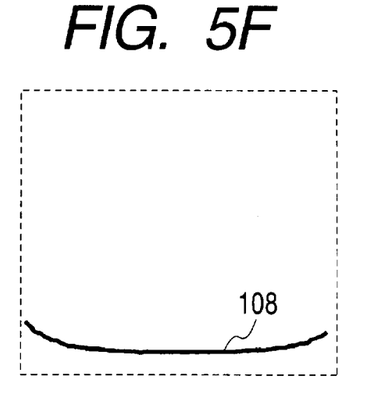

FIGS. 5D, 5E and 5F show an example of image data of a radiation-sensed image having very low levels with almost no sensor sensitivity. A line 106 represents a radiation-sensed image. After the offset 102 is removed from the radiation-sensed image 106, a stable image 107 having almost constant signal values is acquired as shown in FIG. 5E. After the gain correction is performed, an image is rather obtained with noise having a pattern 108 indicative of gain variation or X-ray shading as shown in FIG. 5F.

This noise level is very low, while emphasized in FIG. 5F. Although this noise level is very low, the output image has a large variation since the logarithmic LUT shown in FIG. 4 is used. A general correction method including an offset correction and a gain correction is disclosed, for example, in Japanese Patent Application Laid-Open No. 7-72256. A problem of noise generation caused by the gain correction is not reported.

SUMMARY OF THE INVENTION

It is an object of the invention to solve the above-described problem.

According to the present invention, the foregoing object is attained by providing an apparatus adapted to correct an image data including: (1) an image detector adapted for acquiring the image data and including a plurality of detecting elements for converting X-ray into an image signal; (2) a first correction unit adapted for obtaining an offset-corrected image: (3) a storing unit adapted for storing the offset corrected image to be used for correcting a sensitivity variation of the detecting elements: (4) a second correction unit adapted for correcting a pixel value of the offset-corrected image; and (5) a third correction unit adapted for gain correcting the image signal based on the offset-corrected image, wherein the third correction unit fixes a value of the offset corrected image corresponding to the detecting element of which the image signal indicates a value less than a predetermined value; and a method and computer readable storage medium thereof.

Further, the foregoing object is also attained by providing an apparatus adapted to correct an image data including: (1) an image detector adapted for acquiring the image data and including a plurality of detecting elements for converting X-ray into an image signal: (2) a first correction unit adapted for obtaining an offset corrected image; (3) a storing unit adapted for storing the offset corrected image to be used for correcting a sensitivity variation of the detecting elements; (4) a second correction unit adapted for correcting a pixel value of the offset corrected image; and (5) a third correction unit adapted for gain correcting the image signal based on the offset corrected image, wherein the third correction unit smooths the offset corrected image corresponding to the detecting element of which the image signal indicates a value less than a predetermined value: and a method and computer readable storage medium thereof.

Other objects, features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the descriptions, server to explain the principle of the invention.

DETAILED DESCRIPTION OF THE PREFERRED EMBODIMENTS

Preferred embodiments of the present invention will be described in detail in accordance with the accompanying drawings.

First Embodiment

Figure 1:
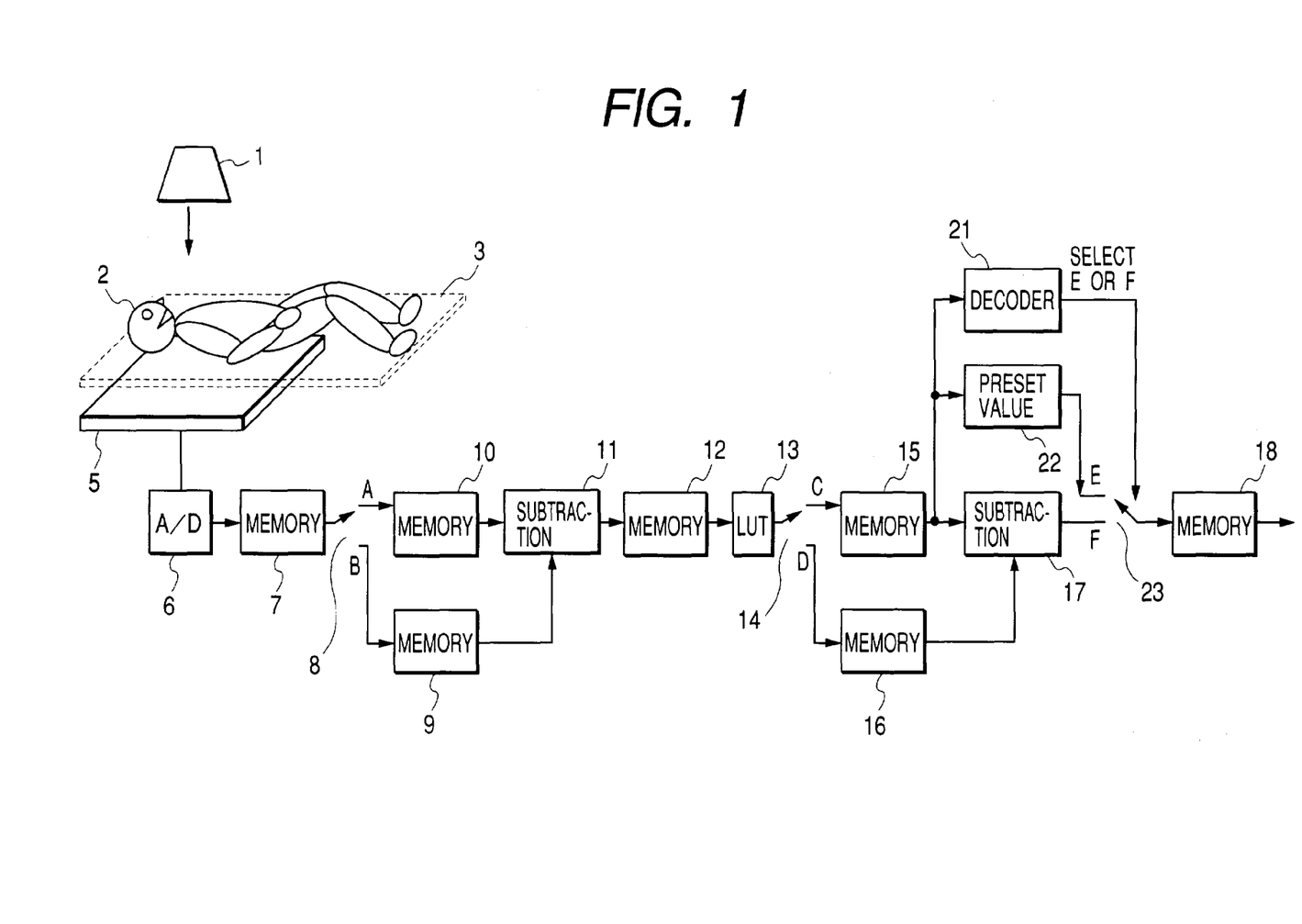
FIG. 1 is a block diagram showing a first embodiment of the invention.

FIG. 1 is a block diagram of a radiographic apparatus embodying the present invention. In FIG. 1, like constituent elements to those shown in FIG. 4 are represented by identical reference numerals and the description thereof is omitted. Different points from the block diagram shown in FIG. 4 are the addition of constituent elements 21 to 23. A decoder 21 evaluates the pixel value offset-corrected and logarithmically converted with a logarithmic LUT to output a signal indicative of whether a gain correction is necessary or not. This signal selects either an E contact or an F contact of a switch 23. The switch 23 selects either a subtraction result F of a subtractor 17 for the gain correction or a value E in place of the subtraction result F. A converter 22 outputs a preset value (pixel value to be replaced with the subtraction result F) to convert the image data supplied from the memory 15, for example.

The converter 22 may be arranged to dump the input data to output a new fixed value or output a value varying in some degree in accordance with the input data.

Figure 6:
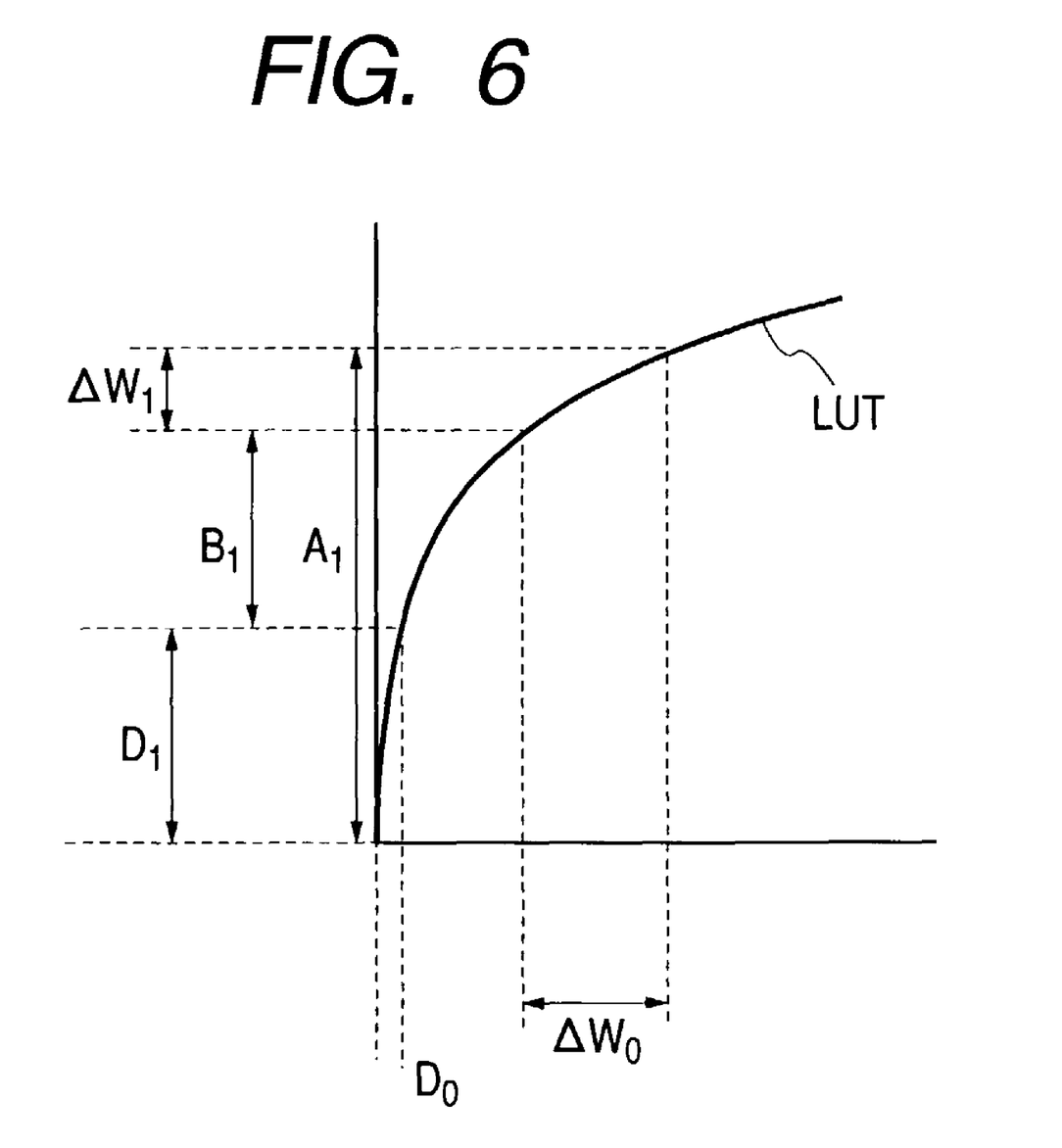
FIG. 6 is a graph used for explaining a preset value of the first embodiment.

A method of determining a preset value will be described with reference to FIG. 6. In FIG. 6, a curve LUT shows the characteristics of the logarithmic conversion LUT. An input data width $\Delta W0$ represents a variation range (a pixel value range of a gain image) of data whose gain variation is to be corrected. An input data D0 indicates that gain correction is not required for the data having a value equal to or smaller than the input data D0, because the sensor linearity cannot be guaranteed for such the value. An input of D0 data yields an output of D1 data. If the value of input data has the value D0 or smaller, the decoder 21 shown in FIG. 1 outputs a signal to select the contact E.

In this case, it is considered reasonable that the preset value is set to a value corresponding to B1 which is the minimum absolute value (subtraction result takes a negative value) of the subtraction result. The reason for this is that since an output range corresponding to $\Delta W0$ is $\Delta W1$, there is a high possibility that an output range of the subtraction of gain correction is from B1 to A1. The converter 22 therefore outputs the value corresponding to B1 independently from the input image data.

Figure 7:
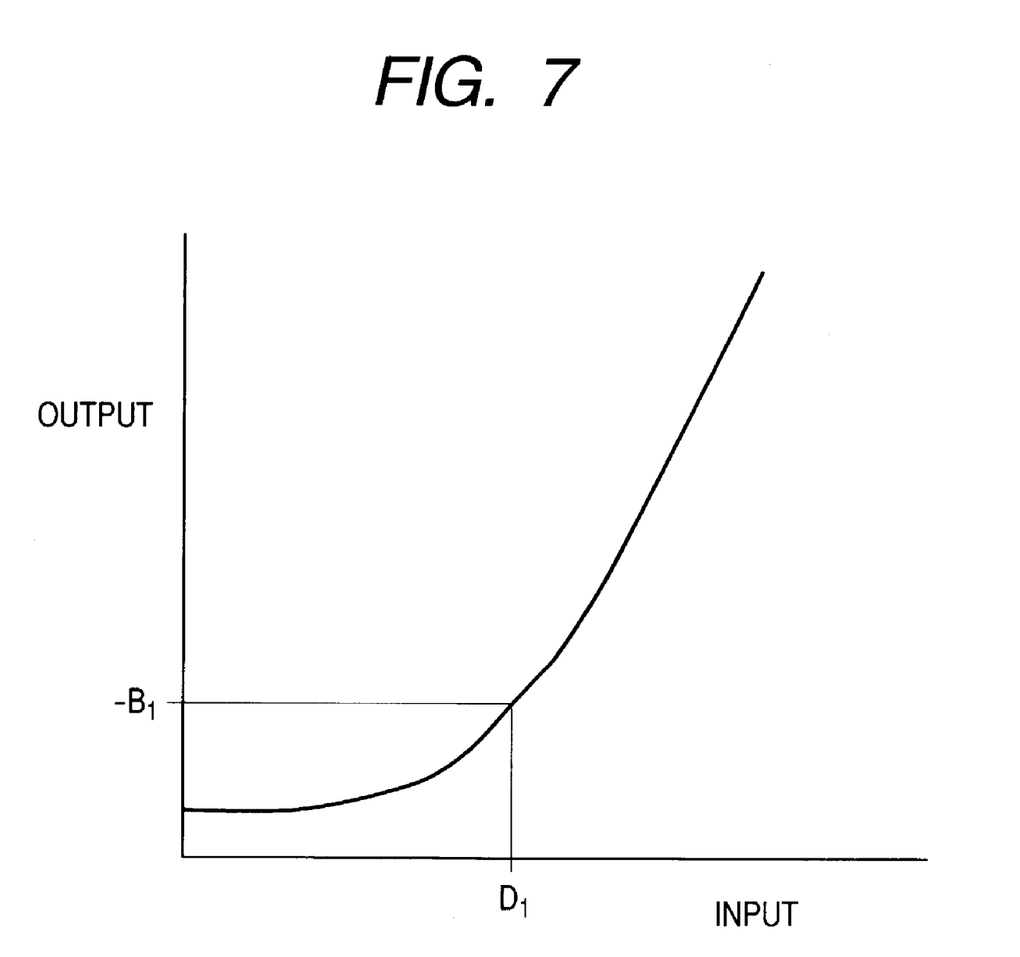
FIG. 7 is a graph showing an example of a LUT of the first embodiment.

Another method is conceivable which estimates a proper output value in accordance with the input image data. For example, the converter 22 is constituted of a LUT such as shown in FIG. 7. This LUT provides an output which changes in some degree with an input. In this embodiment, the decoder 21 evaluates data passed through LUT 13. Since this LUT has a one-to-one correspondence between input and output, the decoder 21 may be arranged so as to evaluate data before it passes through LUT 13.

For example, the decoder 21 outputs a signal instructing to select the contact E if the input (before logarithmic conversion) is 10 or smaller. In this case, a proper low level value is set to the preset value.

The process, judgment and the like of this embodiment can obviously be realized by using a computer and software. It is apparent that the image processing constitution shown in FIG. 1 can be realized by computer programs.

In this embodiment, although a two-dimensional image sensor (X-ray image sensor 5) is used, the embodiment is also applicable to a one-dimensional line sensor.

Second Embodiment

Figure 2:
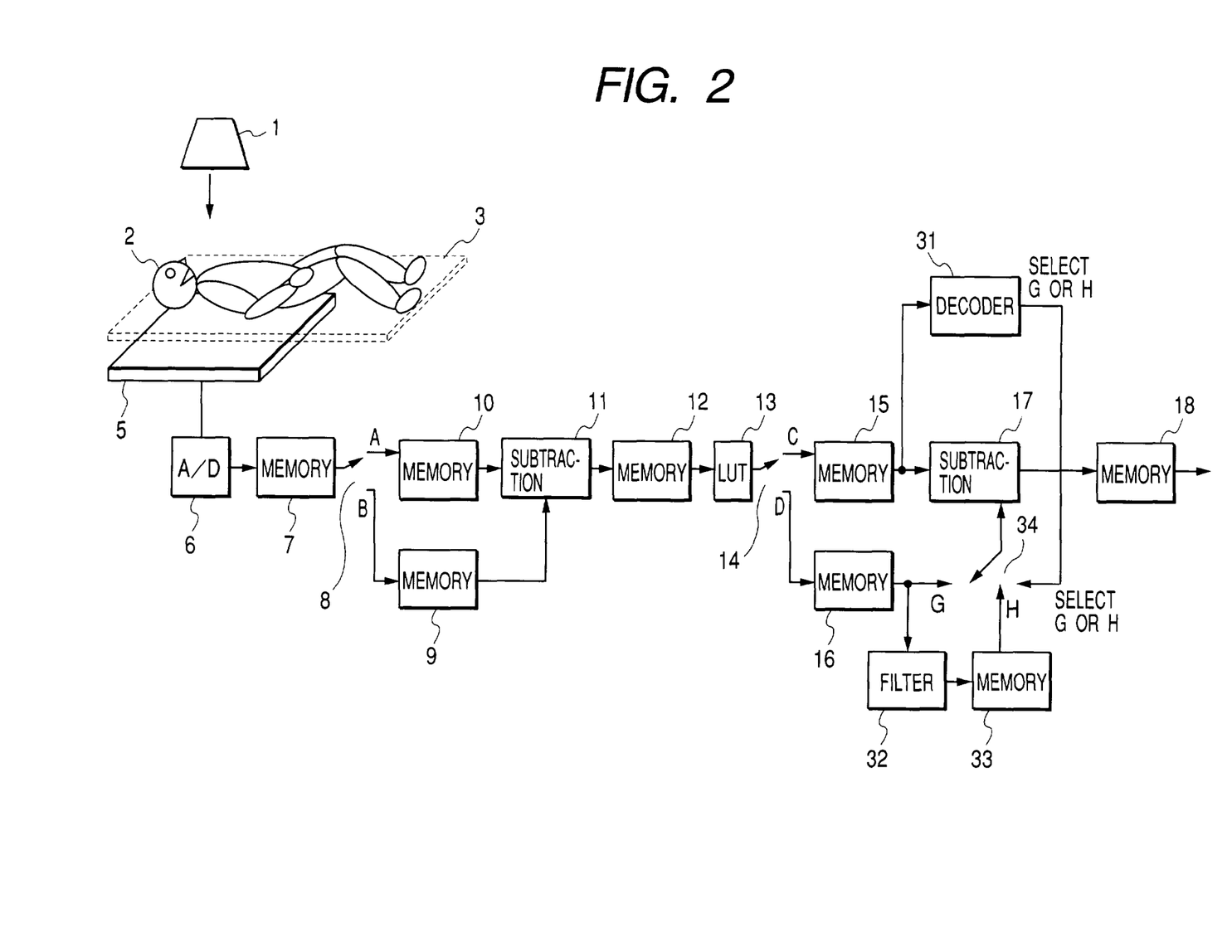
FIG. 2 is a block diagram showing a second embodiment of the invention.

FIG. 2 is a block diagram showing the second embodiment of the invention. Different points from those shown in FIG. 4 are the addition of constituent elements 31 to 34. A value discrimination decoder 31 performs a similar operation to that of the decoder 21 shown in FIG. 1. In accordance with a discrimination result, the decoder 31 outputs a signal to select either a contact G of a switch 34 or a contact H thereof. A filter 32 for spatial filtering has a function of a smoothing filter (simple moving average) with nuclei of 100×100 or more. This filter 32 gradates gain correction data (gain image) and stores it in a memory 33.

If the pixel value is very low and if a pixel belongs to a pixel value area having no linearity, the decoder 31 and switch 34 operate to perform gain correction by using the correction data stored in the memory 33 which data was obtained by gradating the gain correction data stored in the memory 16 by spatial filtering. In this case, precise gain correction is not performed.

However, better gain correction can be rather attained by using the gradated (smoothed) correction data, because gain variation does not substantially exist in the pixel value area having no linearity and the gain correction is not necessarily required. The technological advantage of this embodiment is that correction noises (to be caused by gain correction) can be removed more naturally because the preset value is not necessary to be set in advance.

In this embodiment, although spatial filtering (moving average) is used for the correction of correction data (gain image), an averaging process of a portion or the whole of correction data may also be used. In this case, the memory capacity can be reduced.

In this embodiment, the decoder 21 evaluates data passed through LUT 13. Since this LUT has a one-to-one correspondence between input and output, the decoder 21 may evaluate data before it passes through LUT 13.

Third Embodiment

In the first embodiment, instead of the gain correction value, the preset value is used for a pixel value in a low pixel value (low radiation ray amount) area. In the third embodiment, if there is a pixel having unnecessary correction noises generated by gain correction because of non-linearity of the input/output characteristics of an image sensor, the correction noises are removed by filtering the image after gain correction instead of replacing the pixel value with a preset value. A judgment of whether there is linearity or not is performed by evaluating pixel values before the gain correction.

Figure 3:
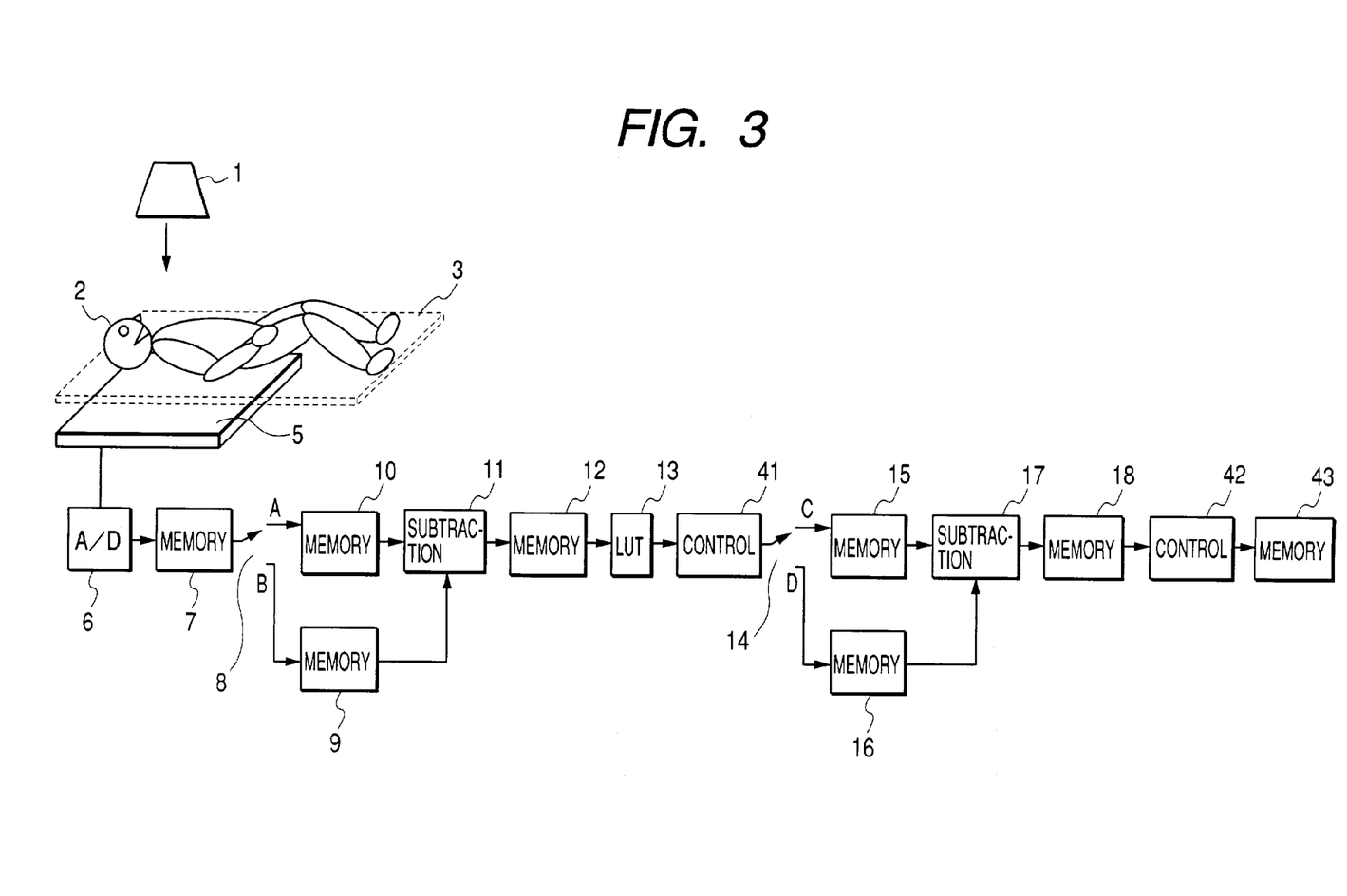
FIG. 3 is a block diagram showing a third embodiment of the invention.
Figures 8A, 8B, 8C:
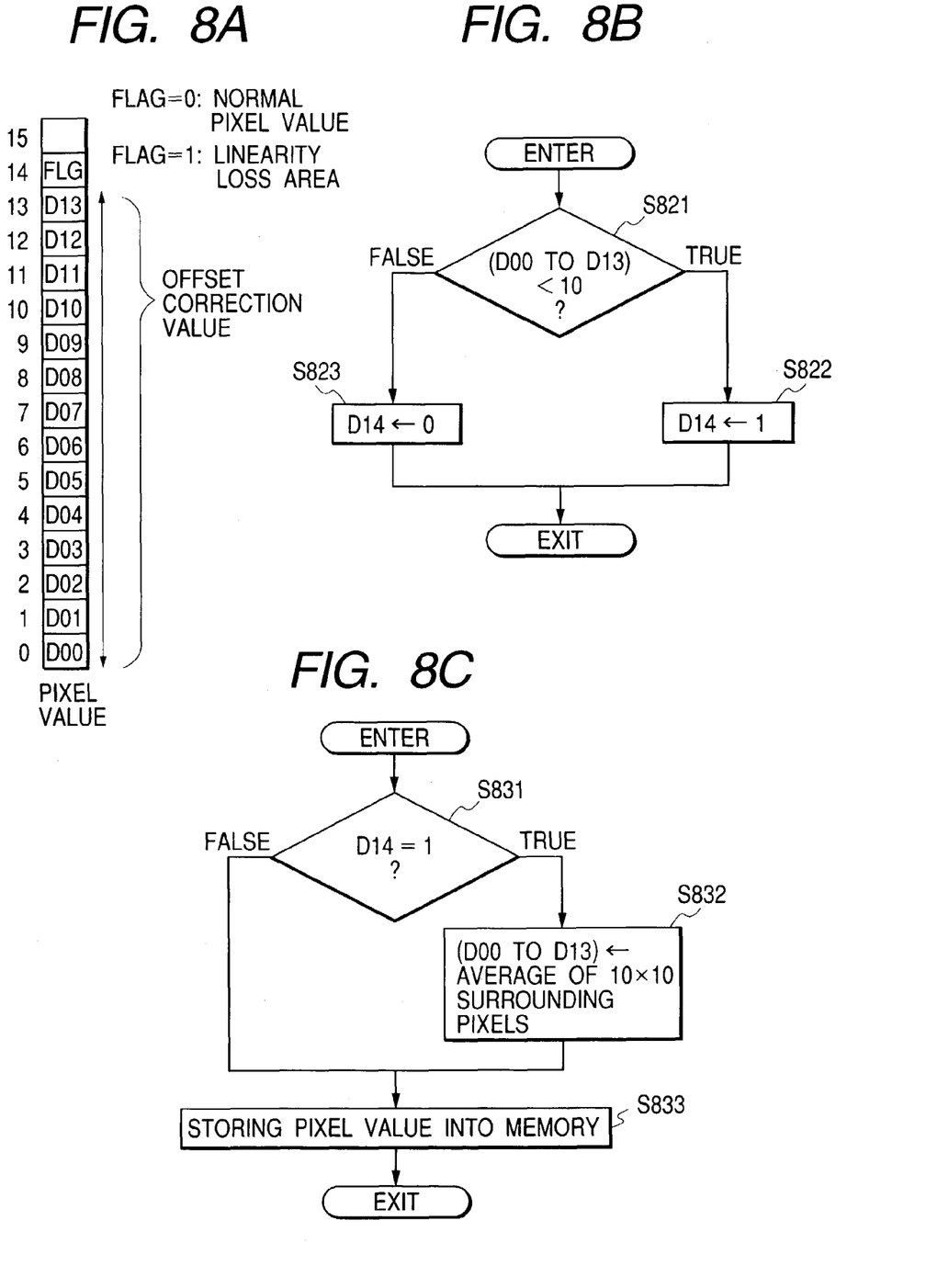
FIGS. 8A, 8B and 8C are diagrams used for explaining the third embodiment.

FIG. 3 is a block diagram of the third embodiment. Substantial different points from those shown in FIG. 1 are the addition of a first controller 41, a second controller 42 and an image memory 43. The operation of each controller is illustrated in FIGS. 8A, 8B and 8C. FIG. 8A shows the bit map of a pixel value according to the third embodiment. Each pixel value is represented by data of a 14-bit width (0-th to 13-th bits).

In this embodiment, a memory element is constituted of 16 bits (2 bytes) and a flag FLG is set to the unused 14-th bit. The flag "0" indicates a normal pixel value, and the flag "1" indicates a pixel value in an area having no linearity. Namely, the flag "1" suggests the generation of correction noises by gain correction. It is difficult to judge from only a pixel value after gain correction whether this pixel corresponds to the radiation ray amount in the area having linearity, because the pixel value was changed due to the gain correction (this pixel value cannot be used as an index of received radiation ray amount).

The first controller 41 shown in FIG. 3 is operated to evaluate a pixel value before gain correction to set the flag. This operation is illustrated in the flow chart of FIG. 8B. A pixel value is checked (step s821). If the pixel value is smaller than 10, it is judged that there is no linearity (the pixel value corresponds to the area without linearity), and the flag FLG is set to "1" (step s822). If it is judged that there is linearity, the flag FLG is set to "0" (step s823).

After this operation by the first controller 41, gain correction including subtraction is performed. The image after gain correction is transferred to the succeeding stage with the flag FLG at D14 being retained, and then is stored in the memory 18. The second controller 42 evaluates the retained D14 (FLG) to determine whether a correction noise removal process is to be executed. Correction noises are removed by spatial filtering which outputs an average value of pixels surrounding a subject pixel. This operation is illustrated in the flow chart of FIG. 8C.

First, D14 is evaluated (step s831). If it is judged that D14="1", i.e., correction noises were generated by gain correction because of loss of linearity, an average value of pixels surrounding the subject pixel, e.g., 10×10 pixels, is written in the succeeding memory 43 (step s832). If it is judged as a normal state (D14="0"), the pixel value of the subject pixel is written in the memory 43 (step s833). An image written in the memory 43 in the above manner is a final output image.

In this embodiment, the evaluation result of data before gain correction is retained at the succeeding process stage. Therefore, the second controller 42 may output the preset value similar to that of the first embodiment, instead of the average value (moving average value). With this arrangement, the effects similar to those of the first embodiment can be attained.

As described above, pixel data immediately after offset correction or data as an index of radiation ray amount is evaluated to identify a low level pixel value which does not show linearity of an image sensor. For such a pixel value, the gain correction is not performed, while modified gain correction data (gain image) is used or an image after gain correction is corrected. In this manner, it is possible to remove artifacts such as noises generated by gain correction. It is important to select a gain correction method in accordance with the data which may be an index of radiation ray amount, such as input data to the gain correction unit.

It is effective to fix pixel data not subjected to gain correction to the preset value such as the minimum value of image data. When a low level pixel value is clipped, the image after gain correction is often clipped. However, if an image after gain correction is clipped, a variation in pixel values increases through the gain correction so that it is difficult to judge whether a pixel value correspond to a level (range) having no linearity of the image sensor. Such a problem can be solved by making a judgment by using data which may be an index of radiation ray amount, such as a pixel value before gain correction.

Other Embodiments

It is needless to say that the object of the invention can be achieved, by supplying a storage medium storing software program codes realizing the function of an apparatus or system of any one of the first to third embodiments to the apparatus or system, and by making a computer (CPU, MPU or the like) of the apparatus or system read and execute the program codes stored in the storage medium.

In this case, the software program codes themselves read from the storage medium realize the function of any one of the first to third embodiments. Therefore, the storage medium storing the program codes and the program codes themselves constitute the present invention.

The storage medium for storing such program codes may be a ROM, a floppy (registered trademark) disk, a hard disk, an optical disk, a magneto-optical disk, a CD-ROM, a CD-R, a magnetic tape, a nonvolatile memory card or the like.

It is obvious that the embodiments of the invention include not only the case that the function of any one of the first to third embodiments is realized by executing the program codes read by a computer but also the case that the function of any one of the first to third embodiments is realized by performing a portion or the whole of actual processes in accordance with the instructions of the program codes and by utilizing an OS or the like running on the computer.

It is obvious that the embodiments of the invention include the case wherein the function of any one of the first to third embodiments is realized by writing the program codes read from the storage medium into a memory of a function expansion board inserted into a computer or of a function expansion unit connected to the computer, and thereafter by making a CPU or the like of the function expansion board or function expansion unit execute a portion or the whole of actual processes.

If the invention is applied to such a program or a storage medium storing the program, the program is constituted of, for example, program codes corresponding to the flow charts shown in FIGS. 8B and 8C.

Many widely different embodiments of the present invention may be constructed without departing from the spirit and scope of the present invention. It should be understood that the present invention is not limited to the specific embodiments described in the specification, except as defined in the appended claims.

What is claimed is:

1. An apparatus adapted to correct image data comprising:
an image detector including a plurality of detecting elements for converting X-rays into an analog image signal;
an A/D converter adapted for digital-converting the analog image signal and obtaining image data;
a storing unit adapted for storing gain data indicating conversion efficiencies of the detecting elements; and
a correction unit adapted for correcting the image data based on the gain data,
wherein, in a case in which a pixel value of the image data indicates a value equal to or greater than a predetermined value, the correction unit corrects the pixel value using the gain data, and
in a case in which the pixel value of the image data indicates a value less than the predetermined value, the apparatus retains the pixel value as a pixel datum without subjecting the pixel value to gain correcting.

2. An apparatus according to claim 1, wherein the correction unit changes the pixel value by using a predetermined reference table.

3. A method adapted to correct image data comprising the steps of:
acquiring an analog image signal by an image detector including a plurality of detecting elements for converting X-rays into an image signal;
digitally converting the analog image signal by means of an A/D converter to obtain the image data;
obtaining from storage gain data indicating conversion efficiencies of the detecting elements; and
performing a correction adapted for correcting the image data based on the gain data,
wherein, in a case in which a pixel value of the image data indicates a value equal to or greater than a predetermined value, the correction step includes correcting the pixel value using the gain data, and
in a case in which the pixel value of the image data indicates a value less than the predetermined value, the pixel value is retained as a pixel datum without being subjected to gain correcting.

4. A non-transitory computer-readable storage medium storing a program for making a computer perform a method adapted to correct image data, the method comprising the steps of:
acquiring an analog image signal by an image detector including a plurality of detecting elements for converting X-rays into an image signal;
digitally converting the analog image signal by means of an A/D converter to obtain the image data;
obtaining from storage gain data indicating conversion efficiencies of the detecting elements; and
performing a correction adapted for correcting the image data based on the gain data,
wherein, in a case in which a pixel value of the image data indicates a value equal to or greater than a predetermined value, the correction step includes correcting the pixel value using the gain data, and
in a case in which the pixel value of the image data indicates a value less than the predetermined value, the pixel value is retained as a pixel datum without being subjected to gain correcting.

5. An apparatus adapted to correct image data comprising:
an image detector including a plurality of detecting elements for converting X-rays into an analog image signal;
an A/D converter adapted for digital-converting the analog image signal and obtaining image data;
a first storing unit adapted for storing first gain data indicating conversion efficiencies of the detecting elements;
a second storing unit adapted for storing second gain data obtained by filtering the first gain data with a smoothing filter; and
a correction unit adapted for correcting the image data based on the first or the second gain data,
wherein, in a case in which a pixel value of the image data indicates a value equal to or greater than a predetermined value, the correction unit corrects the pixel value using the first gain data, and
in a case in which the pixel value of the image data indicates a value less than the predetermined value, the correction unit corrects the pixel value using the second gain data.

* * * * *